United States Patent [19]

Franetzki et al.

[11] Patent Number: 5,352,118
[45] Date of Patent: Oct. 4, 1994

[54] DENTAL INSTRUMENT HAVING A NOZZLE FOR COOLING

[75] Inventors: Manfred Franetzki, Bensheim; Juergen Wohlgemuth, Darmstadt, both of Fed. Rep. of Germany

[73] Assignee: Siemens Aktiengesellschaft, Munich, Fed. Rep. of Germany

[21] Appl. No.: 991,591

[22] Filed: Dec. 16, 1992

[30] Foreign Application Priority Data

Dec. 19, 1991 [DE] Fed. Rep. of Germany .... 4142113.2

[51] Int. Cl.⁵ .......................... A61C 1/10; A61C 1/02; A61C 1/08
[52] U.S. Cl. ........................................ 433/82; 433/104
[58] Field of Search .................................. 433/82, 104

[56] References Cited

U.S. PATENT DOCUMENTS

| | | |
|---|---|---|
| 1,509,448 | 9/1924 | Skinner . |
| 3,451,134 | 6/1969 | Erickson et al. ............... 433/104 X |
| 3,815,241 | 6/1974 | Lingenhohle et al. ............... 433/82 |
| 3,894,338 | 7/1975 | Loge et al. ............... 433/82 |
| 3,952,416 | 4/1976 | Lingenhöle ............... 433/82 |
| 3,956,826 | 5/1976 | Perdreaux, Jr. ............... 433/104 X |
| 4,277,025 | 7/1981 | Harvey . |
| 4,526,541 | 7/1985 | Hubschmid ............... 433/165 |
| 4,802,852 | 2/1989 | Shea ............... 433/127 |
| 5,078,601 | 1/1992 | Badoz et al. ............... 433/82 |
| 5,167,501 | 12/1992 | Castellini ............... 433/82 |

FOREIGN PATENT DOCUMENTS

| | | |
|---|---|---|
| 373140 | 12/1983 | Austria . |
| 1566274 | 10/1969 | Fed. Rep. of Germany . |
| 2263423 | 7/1973 | Fed. Rep. of Germany ........ 433/82 |
| 2355961 | 5/1974 | Fed. Rep. of Germany . |
| 7812633 | 10/1978 | Fed. Rep. of Germany . |
| 3309512 | 10/1983 | Fed. Rep. of Germany . |
| 3302584 | 7/1984 | Fed. Rep. of Germany . |
| 3408313 | 9/1985 | Fed. Rep. of Germany . |
| 8709591.2 | 11/1987 | Fed. Rep. of Germany . |
| 147545 | 10/1961 | U.S.S.R. . |
| 715009 | 2/1980 | U.S.S.R. . |
| 1237261 | 6/1986 | U.S.S.R. . |
| 1438850 | 11/1988 | U.S.S.R. . |
| 2000051 | 1/1979 | United Kingdom . |

OTHER PUBLICATIONS

Abstract of Japanese Patent 2-149357 of Jun. 7, 1990, *Patent Abstracts of Japan*, vol. 14, No. 397, C-752, Aug. 28, 1990.

*Primary Examiner*—Gene Mancene
*Assistant Examiner*—Cindy A. Cherichetti
*Attorney, Agent, or Firm*—Hill, Steadman & Simpson

[57] ABSTRACT

A dental instrument having an active tool for treating a hard dental substance includes an arrangement for spraying water to cool the preparation location with the water either forming an envelope surrounding the tool or being a finely atomized stream of a solid angle directed onto the preparation location. The volume proportion of cooling air relative to the volume of the water in both versions is not greater than the volume of the water so that the envelope or spray are substantially free of air.

17 Claims, 7 Drawing Sheets

DENTAL INSTRUMENT HAVING A NOZZLE FOR COOLING

BACKGROUND OF THE INVENTION

The present invention is directed to an improvement in a cooling arrangement for a dental instrument which has a tool, for example rotating, oscillating or a laser for mechanically removing hard dental substances.

When treating teeth, particularly given mechanical erosion of hard dental substances with an active tool, such as, for example, rotating, oscillating tools or lasers, it is necessary to adequately cool the preparation location in order to avoid heat damage. At least in the case of all rotating instruments, this cooling currently usually occurs by supplying a water/air mixture as a spray. Examples of these arrangements are disclosed in German DE 23 55 961 and Soviet Union 715009. The spray is thereby produced in one or more nozzles in the head housing of the instrument, wherein a relatively small volume stream of water and a volume stream of air that is far greater in comparison to that of the water, are mixed with one another. The ratio of the volume stream of air to water amounts to approximately 100:1. During a preparation, the air added to the cooling water in this way in a relatively great quantity carries the spray cloud out of the patient's mouth into the adjacent environment as an aerosol. Since the water emerging from the dental unit can already be contaminated with germs and the spray flow is contaminated by entrained germs in the mouth, there is a risk of infecting the environment of the work field with germs and, thus, a risk of a direct burden for the treating personnel and for the following patients as well.

Earlier attempts to cool the tool and the preparation location with a water jet directed onto the tool have been abandoned. It was apparently extremely difficult to direct the water jet exactly onto the preparation location, particularly to direct it thereonto over a duration, taking potential calcification or blockage of the extremely small nozzle opening at the water exit location into consideration. Another reason was that an air pillow is formed around the rapidly rotating tool and the water jet is deflected by this air pillow so that it was not possible to optimally hit and, thus, cool the tool or the preparation location, as well. Cooling by water jet is also disadvantageous insofar as the water jet can rebound at a tooth surface and, thus, strike the attending person.

SUMMARY OF THE INVENTION

An object of the present invention is to provide a means of cooling which will reduce the possibilities of the hygiene problems mentioned hereinabove, and wherein the emergence of an aerosol from the patient's mouth is greatly reduced, but that the problems of cooling by water jet can thereby be overcome.

To accomplish these goals, the present invention is directed to an improvement in a dental instrument having an active tool for treating a hard dental substance, the improvement is that the dental instrument has first means for utilizing water for cooling the preparation location, said first means includes second means for forming a nozzle arrangement that comprises one or more discharge openings, said second means controlling the volume portion of the cooling air to be zero or, at maximum, in the order of magnitude of the water being supplied and the second means providing a nozzle which has the water emerging in the form of a water envelope surrounding the tool.

In another embodiment, the second means is constructed so that the water is finely atomized in the region of a discharge opening of the nozzle and has an output with a solid angle.

The invention is based on the perception that it is mainly the air stream that is responsible for conveying the germs. As an extensive investigation has shown, only an extremely low volume stream and, thus, practically no aerosol cloud emerges from the patient's mouth when cooling is undertaken only with water or, respectively, when the proportion of air is extremely low. The relatively slight volume stream of cooling water that is introduced into the patient's mouth, which volume stream lies in a range from approximately 50 ml/min through 100 ml/min, can usually be easily removed with the assistance of a saliva extractor, as a result whereof the extraction with a high-volume extraction cannula, as currently practiced, can usually be eliminated. Significant advantages compared to previous cooling arrangements occur in that the cooling is undertaken practically exclusively with water and, on the basis of a suitable design of the discharge opening of the water jet at the nozzle of the handpiece, the water is far more finely and uniformly distributed in a large solid angle around the tool than is possible with individual water jets. As already mentioned, a relatively great volume stream of air for forming the spray is practically eliminated or, respectively, is reduced to such an extent that practically no germs are dislodged by the high flow and are carried out of the patient's mouth with an aerosol cloud. The measures of the invention can be realized in various ways including the following:

a) having the emerging water being distributed around the tool by specific tuyeres or nozzles so that an especially efficient formation of the cooling water will occur;

b) having the water being separated or nebulized in one or more nozzles to form the spray jet;

c) having the water being directed as a stream against an impact surface at which it bursts and is deflected in the direction of the tool as a spray jet; or d) having the water being distributed as a spray jet on the basis of a vibrating or rotating element in the discharge region.

The critical features of the invention are that the spray jet is not produced at the tip of the tool as a result of the motion thereof, such as rotation or oscillation, but is already produced before impinging on the tool or, respectively, on the preparation location.

Other advantages and features of the invention will be readily apparent from the following description of the preferred embodiments, the drawings and claims.

DESCRIPTION OF THE PREFERRED EMBODIMENTS

Figure 1:
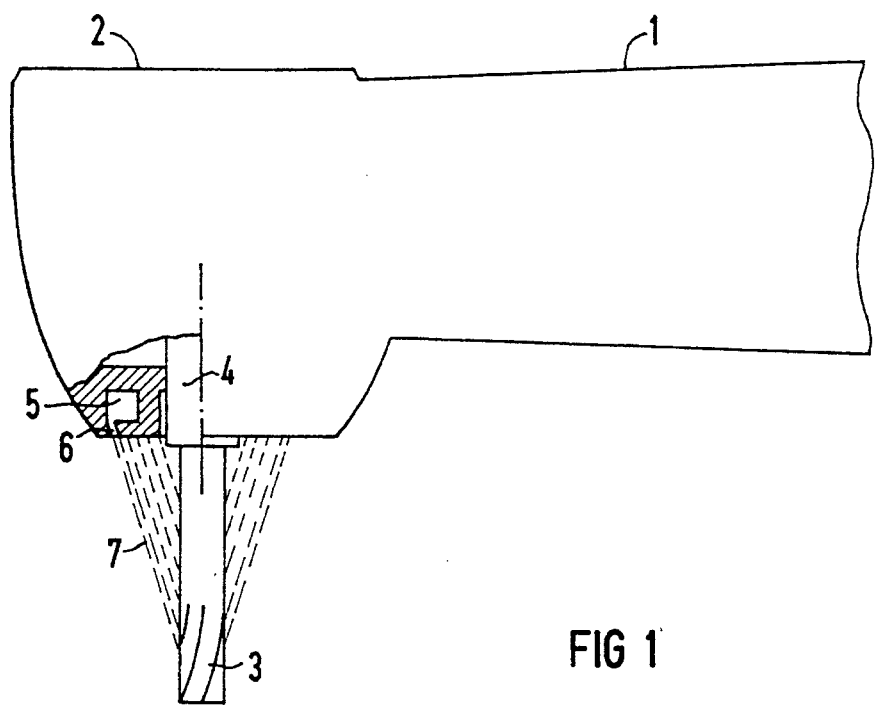
FIG. 1 is a side view of a head housing of a dental handpiece with portions broken away to illustrate the cooling means of the present invention.
Figure 2:
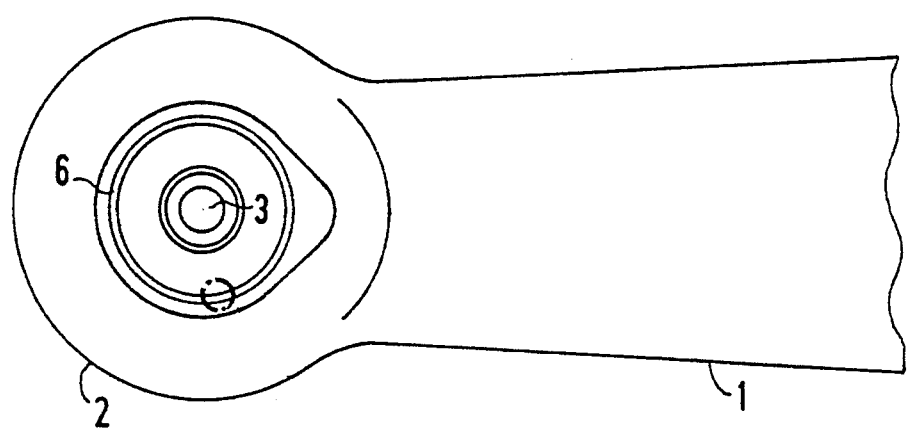
FIG. 2 is a bottom plan view of the head housing of FIG. 1.
Figure 2A:
FIG. 2a is an enlarged portion of the annular gap of the device of FIG. 2.

The principles of the present invention are particularly useful when incorporated in a dental instrument 1 of FIGS. 1 and 2, which has a head housing 2 and a drilling tool 3 which is carried by a drive shaft 4 mounted for rotation in the head housing 2. The agents required for the drive of the tool 3, as well as for cooling the preparation location are brought to the head housing 2 in a known manner. The cooling water is introduced under optimally high pressure into an annular channel 5, which concentrically surrounds the drive shaft 4 of the tool 3. This annular channel 5 has a tapering portion in the axial direction to form a narrow annular gap 6. The annular gap 6 forms a nozzle discharge opening for a thin water envelope 7 that cortically surrounds the tool 3. The water envelope is, thus, structured in a jet shape. The desired, uniform water distribution of the water envelope is assured or, respectively, stabilized, even given lower water pressure as a result of a comb-shaped edge part 8, best illustrated in FIG. 2a, of the inner or the outer diameter of the water discharge nozzle, which part 8 will divide the annular gap 6 into annular segments 8a.

Instead of a conical fashioning of the water envelope 7, a cylindrical water envelope can also be produced with a suitable shaping of the nozzle discharge opening. This cylindrical water envelope should expediently emerge relatively close to the tool shaft 4 at the head housing 2 in order to obtain the desired cooling effect at the preparation location. The water envelope is expediently a water envelope closed on its circumference, however, it is conceivable and lies within the scope of the invention to multiply interrupt the water envelope at its circumference to, thus, allow the water to emerge in the form of clippings or sectors from a conical or cylindrical form. Alternatively to the two shapes of a water envelope which have been disclosed, other geometrical shapes of a construction of a water envelope are also conceivable. For example, the water envelope may have the form of a polygon or parts thereof in cross section.

Thus, the annular gap 6 with the interruptions 8 form second means providing a nozzle for forming an envelope of water surrounding the tool 3, which envelope of water has substantially zero amount of air or, if it does have air, has air of the same order or volume as the water.

Figure 3:
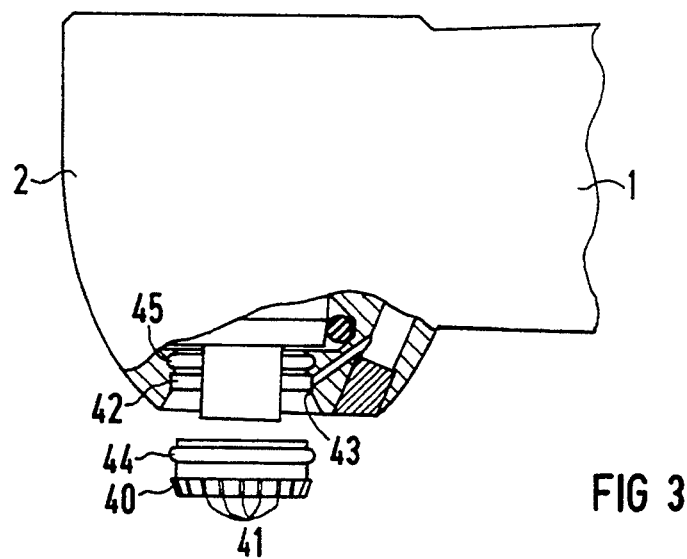
FIG. 3 is a side view of a dental handpiece head housing with portions broken away showing another embodiment of the cooling means of the present invention.
Figure 4:
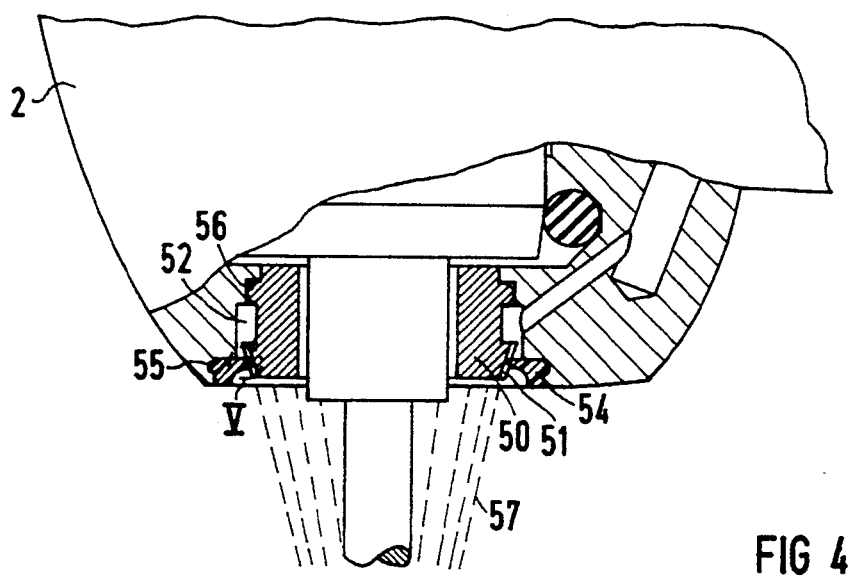
FIG. 4 is a partial side view of a dental handpiece head housing illustrating a third embodiment of the cooling means of the present invention.

An embodiment of the means for forming the envelope is illustrated in FIG. 3 and involves a concentric nozzle insert part 40, which is held at the end face of the head housing 2 of the instrument 1 in an easily detachable fashion. The insert part 40 is shown in the removed condition and comprises a plurality of open distributor channels 41 on a circumferential portion thereof. These distributor channels 41, together with an annular channel 42 and a housing surface 43 in the head housing 2, form a discharge opening for the cooling water. Toward the inside of the head housing, the insert part 40 is provided with a seal ring 44 that corresponds with a correspondingly fashioned annular channel 45 in the head housing 2. The seal ring 44 and annular channel 45 are fashioned so that they simultaneously serve the purpose of holding the insert part in the head housing 2. The housing surface 43 proceeds obliquely outward from the discharge opening, as a result whereof a space that, among other things, facilitates cleaning of the channels and/or, respectively, opposes a blockage, is formed between the insert part and the head housing.

Figure 5:
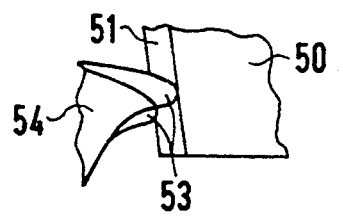
FIG. 5 is an enlarged view illustrating an elastic ring used in the embodiment of FIG. 4.

In a modification of this means for forming a water envelope, an insert part 50, similar to the part 40, is used. The part 50 has open distributor channels 51 that, together with the annular channel 52, form discharge openings for the cooling water. The discharge openings herein are fashioned so that a water envelope 57 is directed onto the preparation location and concentrically forms around the tool shaft. In the unpressurized condition, the discharge openings are closed by elastic sealing lips 53 (best illustrated in FIG. 5) of an additional insert part 54, which is removably held in the head housing 2. The elasticity of the sealing lips are dimensioned so that the sealing lips 53 do not release or open the discharge openings until they are charged with pressure. This achieves the advantage that no undesirable particles can penetrate into the cooling agent line from the outside. A calcification and a blockage can be effectively opposed with this particular embodiment. The insert part can also be screwed into the head housing; however, the illustrated pluggable embodiment has the advantage of significantly simpler manipulatability. It is especially advantageous when the insert parts are composed of a material having relatively poor adhesive properties for lime and dirt. An example of such a material is PTFE, which is a polytetrafluoroethylene. In addition, the insert parts can be composed of an elastic material, at least in the region of the water discharge, for example of silicone rubber, whereby lime or dirt which has potentially adhered can be easily dislodged due to the elastic deformation of the part 54. Finally, the insert parts, as shown, can already be provided with applied annular beads, such as a bead 55 for the part 54 and a bead 56 for the part 50. These beads will cause a fastening or, respectively, sealing of the parts in the housing 2.

In the embodiments of FIGS. 1-5, the second means for forming an orifice forms an envelope surrounding the tool. The second means for forming the orifice can also form one or more streams having a solid angle so that the water can be brought to the preparation location finely atomized by a suitable atomization means in the region of the discharge opening in accordance with another modification.

Figure 6:
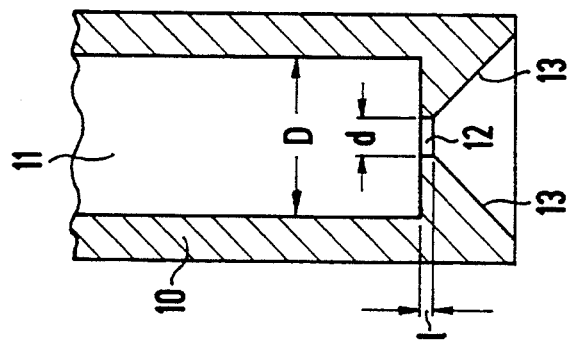
FIG. 6 is a partial cross sectional view of an end of a nozzle in accordance with the present invention.

Five possibilities of atomization of the cooling water are shown in FIGS. 6-10, wherein a nozzle 10 can be arranged in the head housing 2 or in an adjacent neck part of the instrument as a separate component part or as an integral component part. In the embodiment of FIG. 6, the cooling water flows into an antechamber 11 of the nozzle 10 and is forced into the form of a spray jet, in that the water is pressed from the antechamber 11 through a nozzle aperture 12 with optimally high pressure. The diameter d or, respectively, the cross section of the nozzle aperture 12 is extremely small in comparison to the diameter D or, respectively, the cross section of the antechamber 11. In addition, the length I of the aperture 12 is, likewise, extremely short so that the formation of a laminar flow through the nozzle opening 12 is suppressed and the emerging cooling water is atomized or, respectively, nebulized, due to turbulence. As is also the case in the embodiments set forth hereinafter, preferably conically fashioned radiating surfaces 13 are provided following the nozzle aperture 12.

Figure 8:
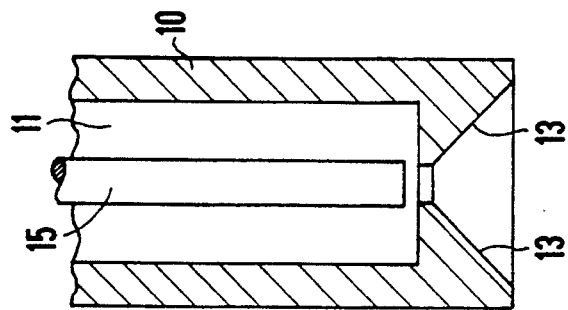
FIG. 8 is a partial cross sectional view of a second embodiment of the nozzle of FIG. 6.
Figure 7:
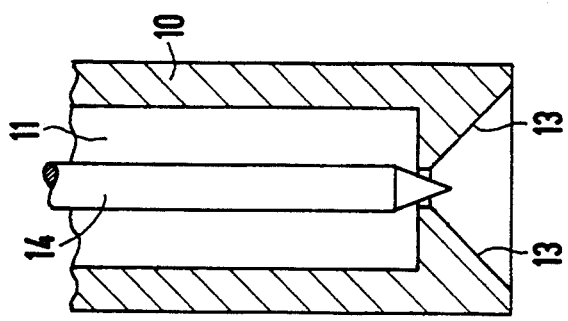
FIG. 7 is a partial cross sectional view of an embodiment of the nozzle of FIG. 6.
Figure 10:
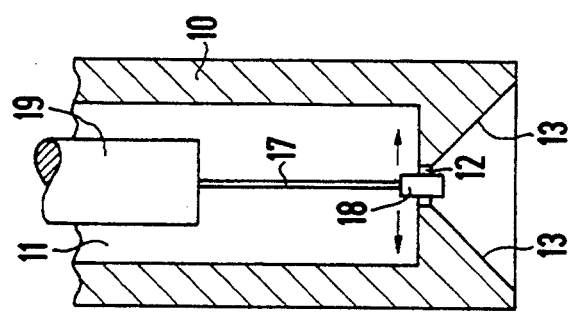
FIG. 10 is a cross sectional view of an end of a fourth embodiment of the nozzle of FIG. 6.
Figure 9:
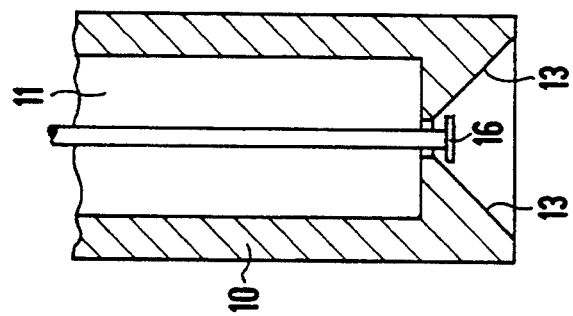
FIG. 9 is a partial cross sectional view of an end of a third embodiment of the nozzle of FIG. 6.

In the embodiments or modifications shown in FIGS. 7 and 8, the atomizing effect is further enhanced in that a valve needle 14 or 15 is arranged in the chamber 11. In the embodiment illustrated in FIG. 7, the tip of the needle 14 is positioned in the aperture 12, while in the embodiment of FIG. 8, the flat end of the needle 15 is positioned immediately in front of the aperture. In the embodiment of FIG. 9, an atomizer plate 16 is attached to the needle, which extends through the opening 12. The plate 16 is arranged following the nozzle aperture. In another modification, the atomizer can be achieved when, as shown in FIG. 10, an elastic valve needle 17 is provided, and this is placed in vibration by the turbulence of the inflowing cooling water, as a result whereof an improvement in the atomization of the water is achieved with the nozzle head 18 positioned in the nozzle aperture 12. Alternatively, an active atomization is also possible in this arrangement by the needle 17 being placed in vibration by an active vibrator generator 19, which, for example, is in the form of an ultrasound generator.

Figure 11:
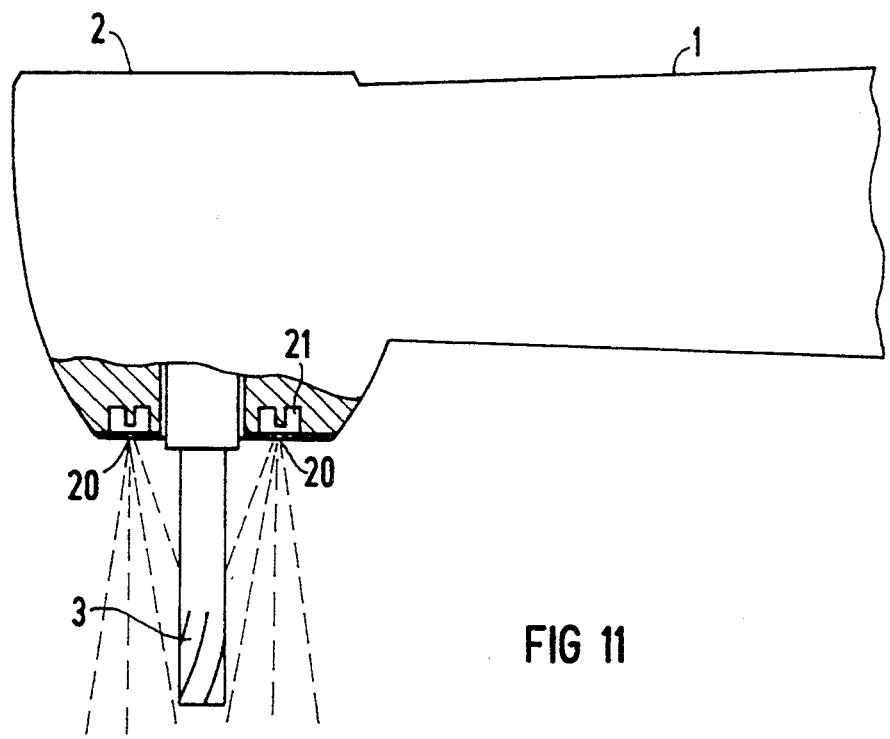
FIG. 11 is a partial side view of a dental handpiece adjacent the head housing with portions broken away to illustrate a fifth embodiment of the cooling means of the present invention.
Figure 12:
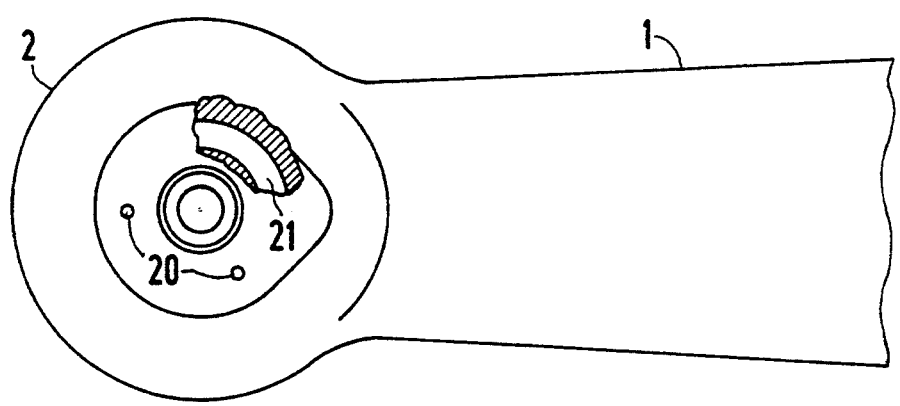
FIG. 12 is a partial bottom plan view of the arrangement of FIG. 11 with portions broken away for purposes of illustration.

In the embodiment illustrated in FIGS. 11 and 12, a plurality of the atomizer nozzles 20 are concentrically arranged around the tool 3 on an underside of the head housing 2, which faces toward the tool. These atomizer nozzles 20 correspond to the principles shown for the embodiment of FIG. 6, and are connected to an annular antechamber 21 that is, likewise, concentrically arranged. In accordance with the described atomizing principle, a plurality of conical spray jets are directed onto the tool tip or, respectively, on the preparation location, and are generated by the flow through the nozzle openings 20.

Figure 13:
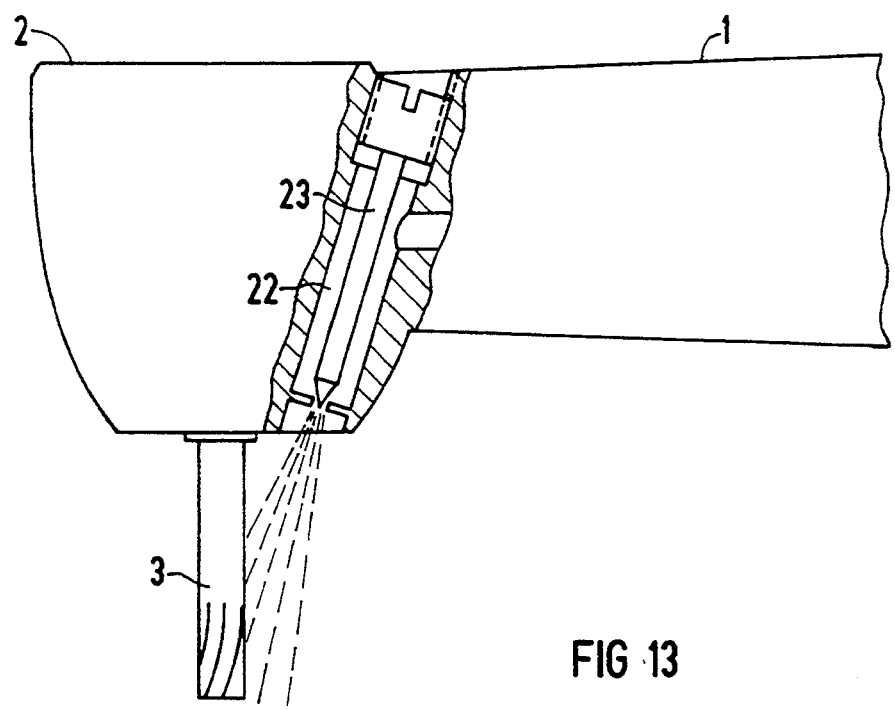
FIG. 13 is a side view of a dental handpiece head housing having a nozzle similar to the embodiment of FIG. 7.

With the embodiment of the nozzle of FIG. 7, a single nozzle atomizing arrangement in the form of a valve needle 23 arranged in an obliquely proceeding channel 22 corresponding to the antechamber 11 is provided in the neck region of the handpiece I (see FIG. 13). The valve or needle 23 here is screwed into the head housing 2 with an appropriate thread at an end facing away from the nozzle aperture so that the conical end can be adjustably changed by axial movement of the element 23 from the outside. This arrangement is also especially maintenance-friendly, since the needle 23 can be screwed out for cleaning the nozzle.

Figure 14:
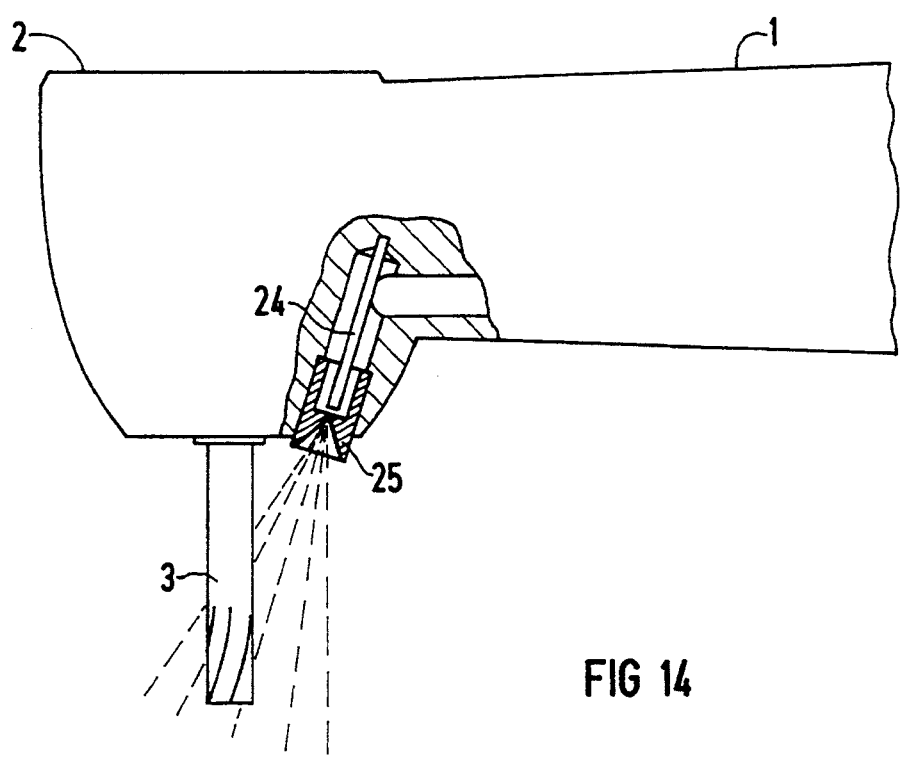
FIG. 14 is a side view of a head housing of a dental handpiece having a modification of the nozzle arrangement of the nozzle of FIG. 8.

Whereas the valve needle is adjustable and the tuyere connection that contains the nozzle aperture is rigidly arranged in the head housing in the embodiment set forth in FIG. 13, the valve needle 24, as illustrated in FIG. 14, can be rigidly arranged in the housing. The tuyere or opening, which is provided in the tuyere connection 25, by contrast, is adjustably threaded into the bore in the housing to adjust the position of the aperture relative to the end of the needle 24.

Figure 15:
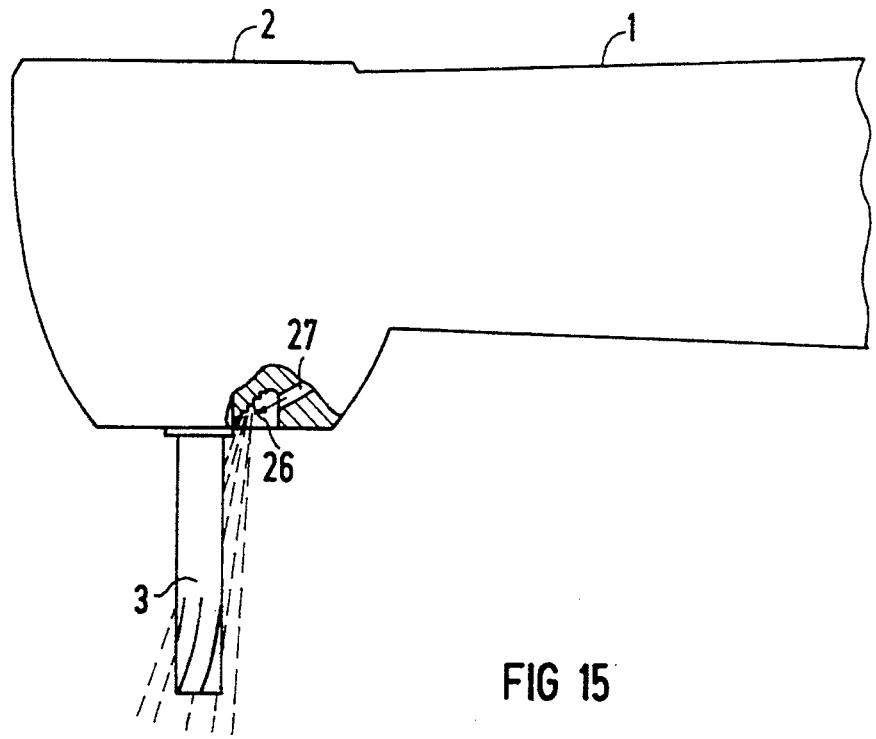
FIG. 15 is a side view of a head housing with portions broken away illustrating another type of cooling arrangement in accordance with the present invention.

In the embodiment according to FIG. 15, an impact surface 26 is provided in the nozzle in the region of the exit location. Cooling water emerging from a channel 27 is directed onto this impact surface 26. The cooling water is atomized at the impact surface 26 and is then deflected in the direction onto the tool 3 in the form of a jet spray. As illustrated, the surface 26 has a rough surface to help break up the spray.

Figure 16:
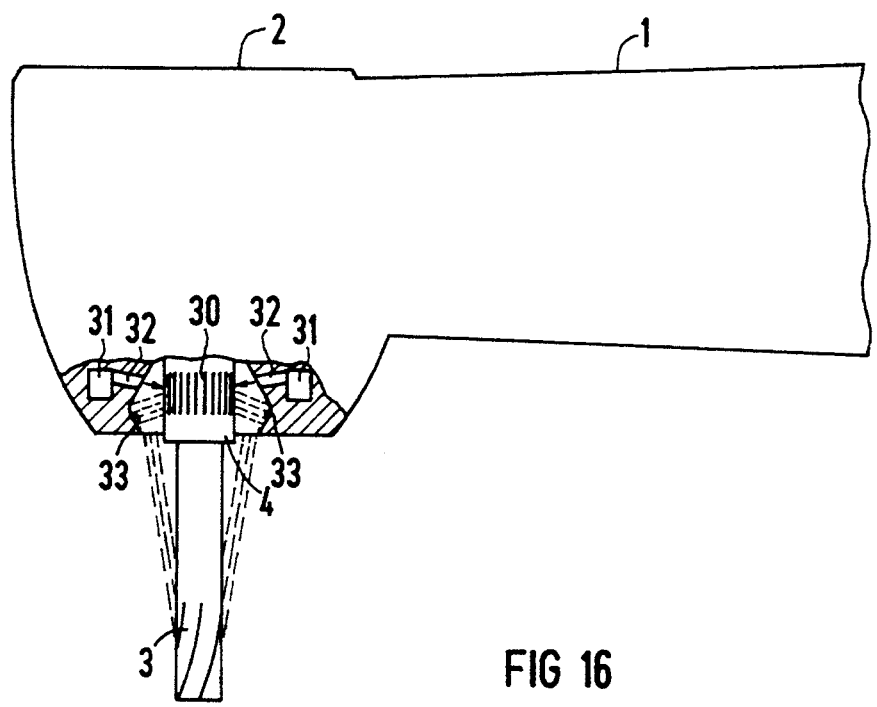
FIG. 16 is a side view of a head housing of a dental handpiece with portions broken away showing yet another embodiment of the cooling arrangement of the present invention.

In another embodiment illustrated in FIG. 16, the drive shaft 4 for the tool 3 is provided with impact surfaces 30, against which the water coming from the annular channel 31 is directed onto the shaft by nozzles 32. As a result of the rotating shaft, the cooling water leaving the nozzles 32 is atomized at the impact or eddy surfaces 30 and is spun toward the outside as a consequence of centrifugal forces so that it is deflected by a conical baffle 33 in the form of a uniform spray jet in a direction toward the tool 3. The baffle 33, as illustrated, is concentrically arranged relative to the rotating surface 30.

Although various minor modifications may be suggested by those versed in the art, it should be understood that we wish to embody within the scope of the patent granted hereon all such modifications as reasonably and properly come within the scope of our contribution to the art.

We claim:

1. A dental instrument having an active tool for treating hard dental substances, the improvement comprising first means for utilizing water for cooling the preparation location, said first means including second means for forming a nozzle arrangement comprising a water discharge opening, said second means containing an annular gap having a comb-shaped edge part in the water discharge opening, wherein the volume proportion of cooling air passing through the nozzle arrangement at a maximum lies in the order of the magnitude of the water being supplied, said second means forming a water envelope for surrounding the tool.

2. In a dental instrument according to claim 1, wherein the second means is fashioned so that the water emerges as a water envelope with a closed circumference.

3. In a dental instrument according to claim 2, wherein the second means is fashioned so that the emerging water envelope is a conical envelope.

4. In a dental instrument according to claim 2, wherein the second means forms a cylindrical envelope.

5. In a dental instrument according to claim 1, wherein the second means includes an annular channel in a head housing of the instrument coacting with an insert part, said insert part being detachably held in the head housing.

6. In a dental instrument according to claim 5, wherein the insert part has a plurality of open distributor channels on a circumference of the insert part to form the comb-shaped edge part, said distributor channels coacting with the annular channel and the head housing to form a plurality of water discharge openings when the part is assembled in said housing.

7. In a dental instrument according to claim 6, wherein the second means includes an elastic element positioned adjacent the discharge openings to close the discharge openings and when subjected to a pressure in the nozzle, said elastic element yielding to open each of the discharge openings.

8. In a dental instrument according to claim 6, wherein at least those parts forming the discharge openings are of a shaped elastic material.

9. In a dental instrument having an active tool for treating hard dental substances, the improvements comprising the instrument having first means for providing water for cooling the preparation location, said first means including a second means for forming a nozzle having a discharge opening, wherein a volume proportion of cooling air passing through the nozzle at a maximum being in the order to magnitude of the volume of water being supplied by to the nozzle and said second means producing a finely atomized flow of water in the region of the discharge opening in an output with a solid angle, said second means including a tuyere having an aperture forming the nozzle opening and a valve needle being positioned with an end disposed in said aperture of the tuyere, one of said valve needle and tuyere being rigidly mounted in the instrument and the other being adjustably mounted to enable adjusting the position of the tuyere relative to the end of the valve needle.

10. In a dental instrument according to claim 9, wherein second means includes means which can be brought into movement to provide atomization of the flow of water through said opening.

11. In a dental instrument according to claim 9, wherein the second means includes atomizing means which is part of a dynamic drive for the tool.

12. In a dental instrument according to claim 11, wherein the dynamic drive which is placed in rotation has eddy surfaces, said second means directing the water on said eddy surfaces so that the stream of water will be atomized by the rotating eddy surfaces.

13. In a dental instrument according to claim 9, wherein the second means includes an impact plate and conical baffle, said impact plate being positioned in an exit region of an aperture for the flow of water to deflect the flow through the aperture onto the conical baffle.

14. In a dental instrument according to claim 9, wherein the second means includes an antechamber discharging into a discharge opening, said discharge opening having a cross section extremely small in relationship to the cross section of the antechamber and wherein the effective length of the discharge opening is extremely small.

15. In a dental instrument according to claim 9, wherein the second means includes a conical radiation surface following the nozzle opening.

16. A dental instrument having an active tool for treating hard dental substances, the improvement comprising first means for utilizing water for cooling the preparation location, said first means including second means for forming a nozzle arrangement comprising a discharge opening, said second means including an elastic element positioned adjacent the discharge opening to close the discharge opening and when subjected to a pressure in the nozzle, said elastic element yielding to open the discharge opening, wherein the volume proportion of cooling air passing through the nozzle arrangement at a maximum lies in the order of the magnitude of the water being supplied, said second means forming a water envelope for surrounding the tool.

17. In a dental instrument having an active tool for treating hard dental substances, the improvements comprising the instrument having first means for providing water for cooling the preparation location, said first means including second means for forming a nozzle having a discharge opening, said second means including atomizing means which includes a rotatable part of a dynamic drive for the tool, said rotatable part having eddy surfaces, said second means directing the water on said eddy surfaces so that the stream of water will be atomized by the rotating eddy surfaces wherein a volume proportion of cooling air passing through the nozzle at a maximum being in the order of magnitude of the volume of water being supplied by the nozzle and said atomizing means producing a finely atomized flow of water in the region of the discharge opening in an output with a solid angle.

* * * * *